(12) United States Patent
Sato

(10) Patent No.: US 7,879,080 B2
(45) Date of Patent: Feb. 1, 2011

(54) STENT PLACEMENT DEVICE

(75) Inventor: Masatoshi Sato, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1075 days.

(21) Appl. No.: 11/496,823

(22) Filed: Aug. 1, 2006

(65) Prior Publication Data

US 2006/0276873 A1    Dec. 7, 2006

Related U.S. Application Data

(63) Continuation of application No. PCT/JP2006/308884, filed on Apr. 27, 2006.

(30) Foreign Application Priority Data

Jun. 3, 2005    (JP) .............................. 2005-164805

(51) Int. Cl.
*A61F 2/06*    (2006.01)
(52) U.S. Cl. .................................... 623/1.11
(58) Field of Classification Search ................ 623/1.11
See application file for complete search history.

(56) References Cited

U.S. PATENT DOCUMENTS

| 5,690,643 | A | 11/1997 | Wijay | |
| 2005/0085891 | A1* | 4/2005 | Goto et al. | ................. 623/1.11 |
| 2005/0085892 | A1 | 4/2005 | Goto et al. | |
| 2008/0004685 | A1* | 1/2008 | Seemann et al. | ........... 623/1.11 |

FOREIGN PATENT DOCUMENTS

| JP | 2000-014769 | | 1/2000 |
| JP | 2000014769 | A * | 1/2000 |
| JP | 2000-152985 | | 6/2000 |
| JP | 2004-517652 | | 6/2004 |
| WO | WO 02/32496 A1 | | 4/2002 |
| WO | WO 03/092782 | | 11/2003 |
| WO | WO 2004/110521 A2 | | 12/2004 |

OTHER PUBLICATIONS

European Office Action dated Aug. 25, 2010.

* cited by examiner

*Primary Examiner*—Todd E Manahan
*Assistant Examiner*—Kevin Everage
(74) *Attorney, Agent, or Firm*—Scully, Scott, Murphy & Presser, P.C.

(57)    ABSTRACT

A stent placement device capable of forward/backward operation for adjusting a placement position of a stent in a living tissue and forward/backward operation of an ultrasonic endoscope in a treatment instrument insertion channel is realized by providing a guide tube holding a stent to be placed in an opening formed in a tissue of a body cavity capable of moving forward/backward in the axial direction, a fixing portion provided at a tip end of the guide tube and including a claw portion and a reduced-diameter portion which is changeable between a locked position and a nonlocked position of the stent when the stent is held by the guide tube, and an operation portion for operating a pusher tube or the like operating movement of the stent of the fixing portion between the locked position and the nonlocked position.

5 Claims, 11 Drawing Sheets

STENT PLACEMENT DEVICE

CROSS REFERENCE TO RELATED APPLICATION

This application is a continuation application of PCT/JP2006/308884 filed on Apr. 27, 2006 and claims benefit of Japanese Application No. 2005-164805 filed in Japan on Jun. 3, 2005, the entire contents of which are incorporated herein by this reference.

BACKGROUND OF THE INVENTION

1. Field of the Invention

The present invention relates to a stent placement device for attaching and placing a stent in an opening formed by an opening instrument in an organ located at the depth in a body cavity under observation by an ultrasonic endoscope device.

2. Description of the Related Art

Recently, for a treatment of an organ located at the depth in a body cavity, a pancreatic cyst generated in a pancreas or the like, for example, attachment and placement of a stent at the pancreatic cyst through a gastric wall or a duodenal wall under observation by an ultrasonic endoscope device have been carried out.

An indwelling tube device for placing an indwelling tube, which is a stent, in a pancreatic cyst through a gastric wall or a duodenal wall is proposed in Japanese Patent Laid-Open No. 2000-14769, for example. The indwelling tube device proposed in Japanese Patent Laid-Open No. 2000-14769 has a needle portion with a tip end formed sharply.

This indwelling tube device comprises a tube portion capable of moving forward/backward with respect to a needle portion and covering the needle portion so that the tip end of this needle portion is exposed, and a stent, which is an indwelling tube capable of moving forward/backward with respect to the needle portion protruding from the tube portion, detachably arranged covering the exposed tip end of the needle portion and having one end face brought into contact with the tip end face of the tube portion (hereinafter referred to as a stent).

On the one end face of the stent, a taper portion is formed. A taper portion provided on the front surface side of this taper portion is to insert the stent into a target portion. Also, a taper portion provided on the inner circumferential face side is to provisionally fix the stent at the tip end of the tube portion. That is, the stent is provisionally fixed by friction between the taper portion on the inner circumferential face side of the one end face of the stent and the tip end of the tube portion.

With this indwelling tube device, the stent is inserted into a living tissue together with the needle portion by advancing the tube portion and the needle portion at the same time while the needle portion is protruded from the tip end face of the stent. The stent inserted with the needle portion can be placed at a target portion of the living tissue by pulling the needle portion out of the stent while pressing/holding the stent with the tube portion.

SUMMARY OF THE INVENTION

A stent placement device in a first preferred embodiment of the present invention comprises a holding portion for holding a stent to be placed in an opening formed in a tissue in a body cavity capable of moving forward/backward in the axial direction, a fixing portion provided at the tip end of the holding portion and is changeable between a position at which the stent is locked and a position at which the stent is not locked when the stent is held by the holding portion, and an operation portion for operating change of the fixing portion between the stent locked position and the stent nonlocked position.

The fixing portion may include a lock portion for locking the tip end portion of the stent in the axial direction held by the holding portion.

The fixing portion may include an engagement portion to be engaged with an inner circumferential face of the stent held by the holding portion.

The fixing portion may include an engagement hole provided at the stent held by the holding portion and a lock tube having a lock piece to be engaged with the engagement hole.

The lock portion may include a claw portion provided at the tip end of the holding portion in the axial direction and a reduced-diameter tip end portion whose diameter at the tip end having the claw portion can be reduced with respect to the central axis in the axial direction.

The lock portion may be a turned-up portion which is provided outside the tip end of the holding portion and is deformable at the nonlocked position of the stent.

The lock portion may be a raiser edge unit which is raised outward at the tip end of the holding portion and can be accommodated in the holding portion at the nonlocked position of the stent.

The lock portion may be a bellows portion provided on an outer circumference on the tip end of the holding portion in the axial direction for expanding/contracting an outer diameter of the holding portion in the axial direction.

The engagement portion may be a bellows portion which is provided on the outer circumference on the tip end of the holding portion and whose outer diameter to be brought into contact with the inner circumferential face of the stent is expanded/contracted.

The operation portion may be a pusher tube provided on the outer circumference of the holding portion for moving the stent from the locked position to the nonlocked position of the fixing portion.

The operation portion may be a core which is provided on an inner circumference of the fixing portion and is changeable between the locked position and the nonlocked position of the fixing portion.

The operation portion may be a pulling thread for pulling a raiser edge unit of the lock portion of the fixing portion or a bellows tube for expanding/contracting the bellows portion.

The operation portion may be a release tube for engaging and disengaging the engagement hole of the stent and the lock piece of the lock tube.

A stent placement device in a second preferred embodiment of the present invention comprises an opening instrument inserted into a body cavity for forming an opening in an organ in the body cavity, a stent attached and placed in the opening formed by the opening instrument, a holding portion in which the opening instrument is inserted into an inner circumference and the stent is held capable of moving forward/backward in the axial direction of an outer circumference, a fixing portion which is provided at a tip end of the holding portion and is changeable between a position at which the stent is locked and a position at which the stent is not locked when the stent is held by the holding portion, and an operation portion for operating change of the fixing portion between the locked position and the nonlocked position of the stent.

The fixing portion may include a lock portion for locking the tip end portion of the stent in the axial direction held by the holding portion.

The fixing portion may include an engagement portion to be engaged with an inner circumferential face of the stent held by the holding portion.

The fixing portion may include an engagement hole provided at the stent held by the holding portion and a lock tube having a lock piece to be engaged with the engagement hole.

The lock portion may include a claw portion provided at the tip end of the holding portion in the axial direction and a reduced-diameter tip end portion whose diameter at the tip end having the claw portion can be reduced with respect to the central axis in the axial direction.

The lock portion may be a turned-up portion which is provided outside the tip end of the holding portion and is deformable at the nonlocked position of the stent.

The lock portion may be a raiser edge unit which is raised outward at the tip end of the holding portion and can be accommodated in the holding portion at the nonlocked position of the stent.

The lock portion may be a bellows portion provided on an outer circumference on the tip end of the holding portion in the axial direction for expanding/contracting an outer diameter of the holding portion in the axial direction.

The engagement portion may be a bellows portion which is provided on the outer circumference on the tip end of the holding portion and whose outer diameter to be brought into contact with the inner circumferential face of the stent is expanded/contracted.

The operation portion may be a pusher tube provided on the outer circumference of the holding portion for moving the stent from the locked position to the nonlocked position of the fixing portion.

The operation portion may be the opening instrument which is provided on an inner circumference of the fixing portion and is changeable between the locked position and the nonlocked position of the fixing portion.

The operation portion may be a pulling thread for pulling the raiser edge unit of the lock portion of the fixing portion or a bellows tube for expanding/contracting the bellows portion.

The operation portion may be a release tube for engaging and disengaging the engagement hole of the stent and the lock piece of the lock tube.

DESCRIPTION OF THE PREFERRED EMBODIMENTS

Figure 18:
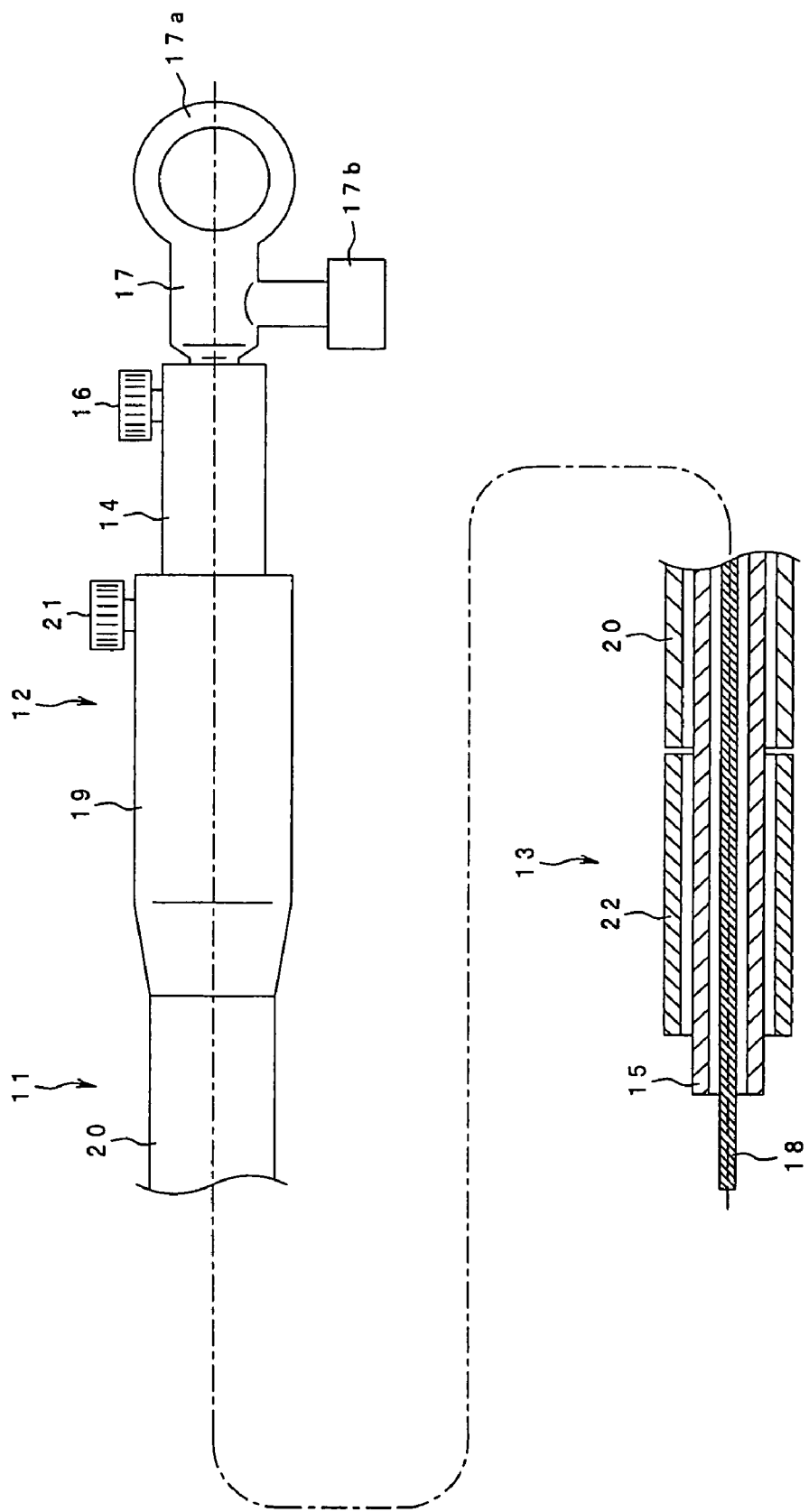
FIG. 18 is an explanatory view for explaining an outline construction of the stent placement device of the preferred embodiment of the present invention.

A preferred embodiment of the present invention will be described below in detail referring to attached drawings. First, referring to FIG. 18, outline construction of a stent placement device of each preferred embodiment of the present invention which will be described below will be explained. A stent placement device 11 of each preferred embodiment of the present invention comprises a handle portion 12 held and operated by an operator, and an insertion portion 13 inserted into a treatment instrument insertion channel of an ultrasonic endoscope device, not shown, to be inserted into a target portion in a body cavity.

The handle portion 12 comprises a substantially cylindrical handle main body 14, an electrode slider 17 loosely fitted on an inner circumference of the handle main body 14 capable of moving forward/backward, a pusher slider 19 loosely fitted on an outer circumference of the handle main body 14 capable of moving forward/backward, an electrode lock screw 16 provided on a side face of the handle main body 14 and a pusher lock screw 21 provided on a side face of the pusher slider 19.

The electrode lock screw 16 is to fix forward/backward slide of the electrode slider 17 with respect to the handle main body 14. Moreover, the pusher lock screw 21 is to fix forward/backward slide of the pusher slider 19 with respect to the handle main body 14.

The electrode slider 17 is provided with a knob portion 17a operated by the operator for forward/backward movement, and a connector portion 17b to which a radiofrequency power device for supplying radiofrequency power to an electrode of an electrode needle 18 forming an opening, which will be described later, is connected.

The insertion portion 13 comprises a guide tube 15 formed relatively flexible by a lengthy resin member whose base end is fixed to a tip end of the handle main body 14 of the handle portion 12, the electrode needle 18 whose base end is fixed to a tip end of the electrode slider 17 of the handle portion 12 and inserted through a hollow portion of the guide tube 15, a pusher tube 20 whose base end is fixed to a tip end of the pusher slider 19 of the handle portion 12 and loosely fitted on an outer circumference of the guide tube 15, and a stent 22 attached by insertion on an outer circumference on the tip end of the guide tube 15 and located at a tip end of the pusher tube 20.

The electrode needle 18 has an electrode provided at a tip end for drilling a hole in a living tissue, and radiofrequency power is supplied from the connector portion 17b of the electrode slider 17.

In the stent placement device 11, when the electrode slider 17 is slid forward/backward with respect to the handle main body 14, the tip end of the electrode needle 18 is moved forward/backward from the tip end of the guide tube 15 in the axial direction of the guide tube 15.

A user can fix the forward/backward moved position of the tip end of the electrode needle 18 from the tip end of the guide tube 15 by tightening the electrode lock screw 16 at a position where the tip end of the electrode needle 18 is moved forward/backward by a predetermined amount from the tip end of the guide tube 15. Also, when the user slides the pusher slider 19 forward/backward with respect to the handle main body 14, the stent 22 attached by insertion at the tip end of the guide tube 15 is pushed out to the tip end of the guide tube 15 from the tip end of the pusher tube 20.

Figure 1:
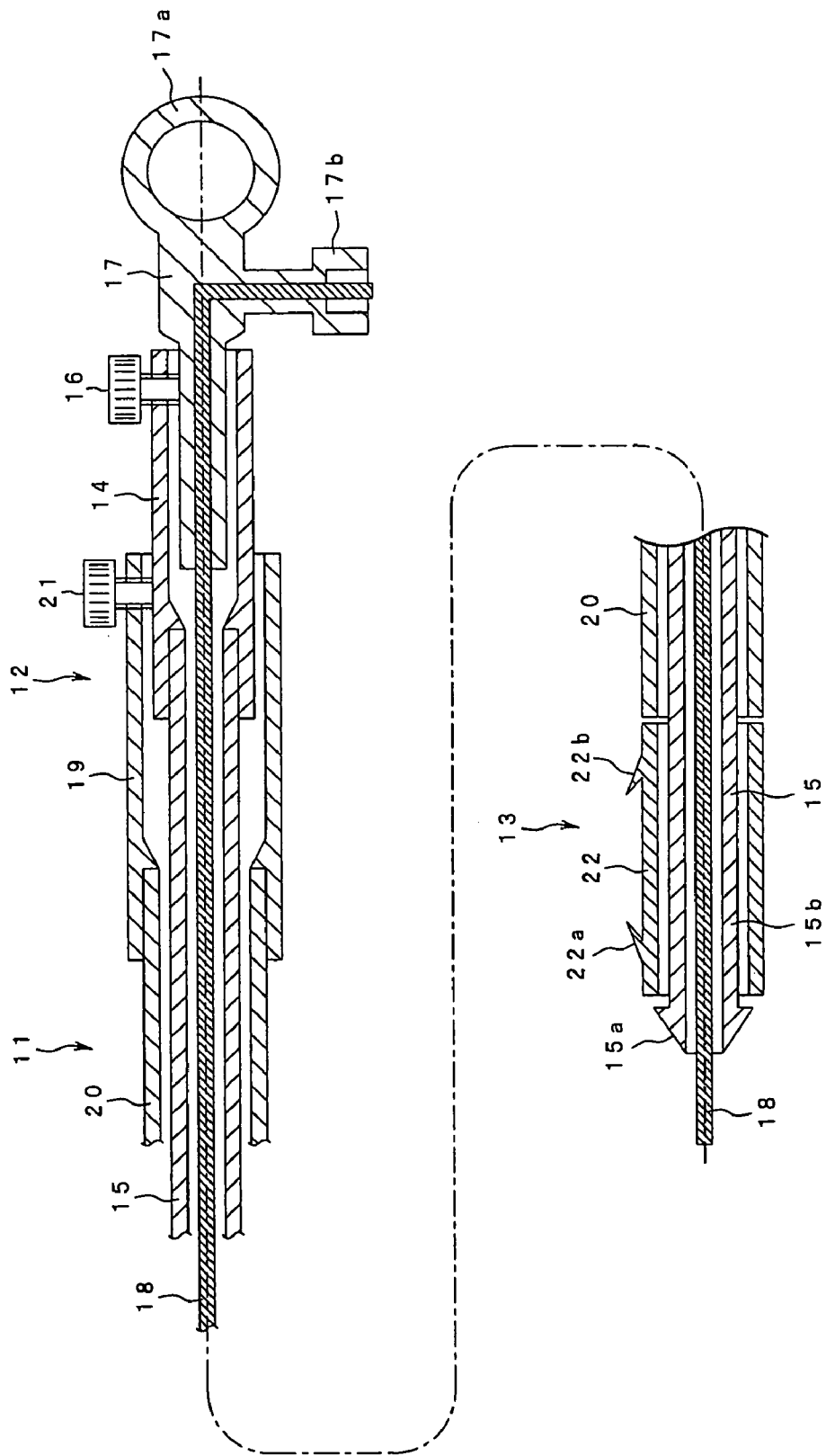
FIG. 1 is a sectional view showing an entire construction of a stent placement device of a first preferred embodiment of the present invention.
Figure 2:
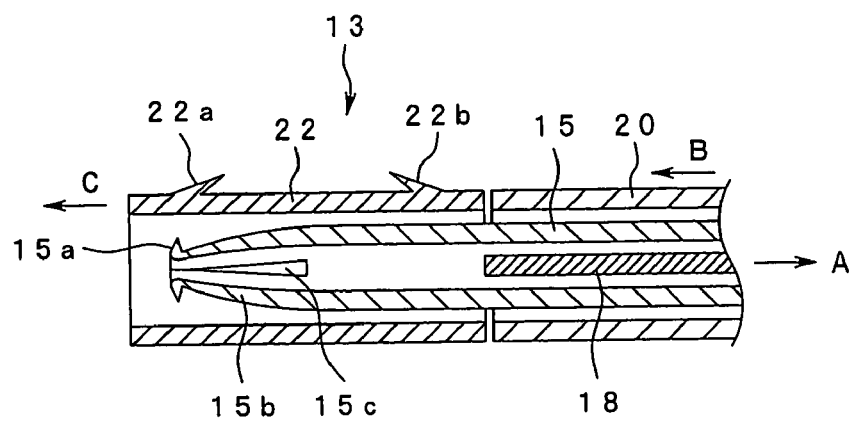
FIG. 2 is a sectional view showing stent placement operation at a tip end of an insertion portion of the stent placement device in the first preferred embodiment of the present invention.
Figure 3:
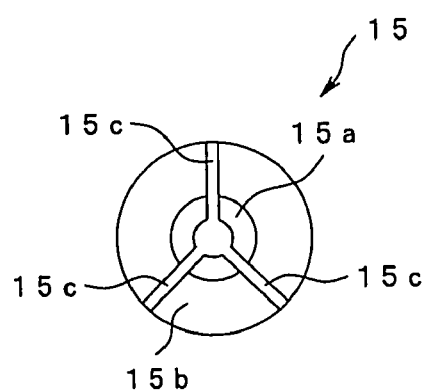
FIG. 3 is a plan view showing a construction at a tip end of a guide tube used for the stent placement device in the first preferred embodiment of the present invention.
Figure 4:
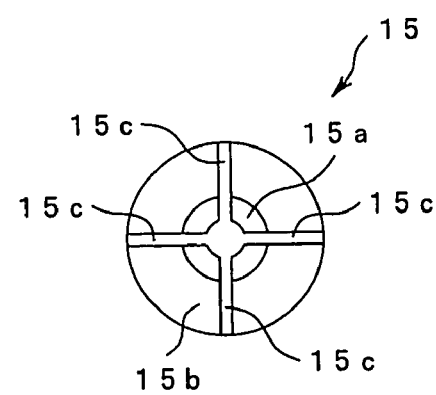
FIG. 4 is a plan view showing a construction at the tip end of the guide tube used for the stent placement device in the first preferred embodiment of the present invention.

A first preferred embodiment of the present invention according to the stent placement device 11 with the above outline construction will be described using FIGS. 1 to 4. According to the first preferred embodiment of the present invention, FIG. 1 is a sectional view showing an entire construction of the stent placement device, FIG. 2 is a sectional view showing a stent placement operation at the tip end of the insertion portion of the stent placement device, FIG. 3 is a plan view showing the construction at the tip end of the guide tube used in the stent placement device, and FIG. 4 shows a variation showing a plan view showing the construction of the tip end of the guide tube used in the stent placement device.

The stent placement device 11 in the first preferred embodiment of the present invention has, as mentioned above using FIG. 18, the handle portion 12 and the insertion portion 13.

The handle portion 12 comprises the handle main body 14 with the tip end to which the base end of the guide tube 15 is fixed, the electrode slider 17 with the tip end to which the base end of the electrode needle 18 to be inserted into the guide tube 15 from the rear end of the handle main body 14 is fixed and loosely fitted on the inner circumference of the handle main body 14 capable of moving forward/backward, and the pusher slider 19 with the tip end to which the base end of the pusher tube 20 loosely fitted on the outer circumference of the guide tube 15 is fixed and loosely fitted on the outer circumference of the handle main body 14 capable of moving forward/backward.

The handle main body 14 is provided with the electrode lock screw 16 for fixing the electrode slider 17. The pusher slider 19 is provided with the pusher lock screw 21 for fixing the pusher slider 19 with respect to the handle main body 14. The electrode slider 17 is provided with the knob portion 17a and the connector portion 17b.

The insertion portion 13 has the electrode needle 18 inserted capable of moving forward/backward into the inner circumference of the guide tube 15 whose base end is fixed to the handle main body 14, the pusher tube 20 loosely fitted capable of moving forward/backward on the outer circumference of the guide tube 15, and the stent 22 attached by insertion to the outer circumference of the tip end of the guide tube 15 and located at the tip end of the pusher tube 20.

The tip end of the electrode needle 18 is operated to move forward/backward to project/sink in the axial direction of the guide tube 15 from the tip end of the guide tube 15 by forward/backward operation of the electrode slider 17. At the tip end of the guide tube 15, a claw portion 15a to lock the tip end of the stent 22 is formed.

Moreover, a reduced-diameter portion 15b is formed in which the tip end of the guide tube 15 is inclined toward the center in the axial direction of the guide tube 15 and the outer diameter is reduced. The diameter of this reduced-diameter portion 15b of the guide tube 15 is, as shown in FIG. 3, reduced since a plurality of slits 15c are provided from the tip end of the guide tube 15 to a predetermined position.

That is, when the electrode needle 18 is inserted into the inner circumference of the guide tube 15 and protrudes from the tip end of the guide tube 15, the reduced-diameter portion 15b of the guide tube 15 is pushed up by the electrode needle 18 to have an outer diameter substantially equal to the base end side of the guide tube 15. Also, when the electrode needle 18 is pulled, sinking from the tip end of the guide tube 15, and pulled out to the base end side from the reduced-diameter portion 15b, the reduced-diameter portion 15b of the guide tube 15 is inclined in the center axial direction and the outer diameter is reduced.

Note that the reduced-diameter portion 15b of the guide tube 15 may be provided with the slits 15c with an interval of 120 degrees when seen from the tip end of the guide tube 15, as shown in FIG. 3, or with an interval of 90 degrees, as shown in FIG. 4. Of course, it is only necessary that the reduced-diameter portion 15b is in the structure of diameter reduction in any methods other than illustrated.

The stent 22 is provided with a pair of turned-up portions 22a, 22b on the outside. These turned-up portions 22a, 22b are to prevent movement when the stent 22 is placed in the living tissue.

When the stent 22 is attached by insertion to the reduced-diameter portion 15b at the tip end of the guide tube 15 and the diameter of the reduced-diameter portion 15b of the guide tube 15 is expanded by insertion of the electrode needle 18, the tip end is locked by the claw portion 15a of the guide tube 15. Also, the rear end of the stent 22 is locked by the tip end of the pusher tube 20 loosely fitted on the outer circumference of the guide tube 15.

Next, operation to place the so constructed stent placement device 11 in the living tissue will be described. The user attaches the stent 22 by insertion on the outer circumference of the reduced-diameter portion 15b at the tip end of the guide tube 15 of the stent placement device 11. After that, the user slides the electrode slider 17 to project the tip end of the electrode needle 18 from the tip end of the guide tube 15 in the axial direction by a predetermined amount. And the user fixes the electrode slider 17 using the electrode lock screw 16.

At this time, the diameter of the reduced-diameter portion 15b of the guide tube 15 is expanded by insertion of the electrode needle 18, and the claw portion 15a locks the tip end of the stent 22. By this, drop of the stent 22 from the tip end of the guide tube 15 can be prevented.

Next, the user slidingly operates the pusher slider 19 till the tip end of the pusher tube 20 is slid and brought into contact with the rear end of the stent 22 attached by insertion in the reduced-diameter portion 15b at the tip end of the guide tube 15 and fixes the pusher slider 19 using the pusher lock screw 21.

By this, the stent 22 is locked in the state held between the claw portion 15a of the guide tube 15 and the tip end of the pusher tube 20.

The stent placement device 11 in the state where the stent 22 is locked between the claw portion 15a of the guide tube 15 and the tip end of the pusher tube 20 is inserted into the body cavity observed by an ultrasonic endoscope device, not shown, through the treatment instrument insertion channel of the ultrasonic endoscope device.

The insertion portion 13 of the stent placement device 11 operates the handle main body 14 forward/backward under an ultrasonic tomographic image of a pancreatic cyst located outside the gastric wall, for example, by the ultrasonic endoscope device to form an opening from the gastric wall to the pancreas by supplying radiofrequency power to the electrode provided at the tip end of the electrode needle 18. And the user operates insertion of the guide tube 15 and the stent 22 attached by insertion to the outer circumference of the guide tube 15 into the opening generated by the electrode needle 18.

In the insertion operation of the guide tube 15 and the stent 22 into the opening generated by this electrode needle 18, when the user inserts the stent 22 deeper than a desired position of the pancreatic cyst, the user pulls out the handle main body 14. Then, the stent 22 can be moved in the direction to be pulled out of the pancreatic cyst since the stent 22 is locked by the claw portion 15a of the guide tube 15.

Next, operation to place the stent 22 inserted to a predetermined position of the pancreatic cyst will be described using FIG. 2. The user loosens the electrode lock screw 16 of the handle portion 12 and slides the electrode slider 17 so as to pull the electrode needle 18 out of the inner circumference of the guide tube 15 in a direction of an arrow A in this figure.

At this time, when the tip end of the electrode needle 18 is pulled out to the base end side at least far from the reduced-diameter portion 15b of the guide tube 15 by sliding of the electrode slider 17, the reduced-diameter portion 15b of the guide tube 15 is inclined toward the center in the axial direction and the diameter is reduced. In this state, when the diameter of the reduced-diameter portion 15b of the guide tube 15 is reduced, the claw portion 15a is removed from the tip end of the stent 22 to release lock of the stent 22.

The user pulls out the electrode needle 18 to a predetermined position and then, loosens the pusher lock screw 21, slides the pusher slider 19 with respect to the handle main body 14 and slides the pusher tube 20 in a direction of an arrow B in this figure.

At this time, by sliding of the pusher tube 20 in the arrow B direction, the stent 22 brought into contact with the tip end of the pusher tube 20 is pushed out from the tip end of the guide tube 15 in a direction of an arrow C in this figure. And the stent 22 is placed at a predetermined position of the pancreatic cyst since the stent 22 has been released from lock by the claw portion 15a of the guide tube 15.

Alternatively, other than the above mentioned operation, the user pulls out and slides the handle main body 14 while the rear end of the stent 22 is locked by the tip end of the pusher tube 20. And when the handle main body 14 is pulled out and slid, since the claw portion 15a of the guide tube 15 has been removed from the tip end of the stent 22, the stent 22 can be pulled out of the guide tube 15 at a position locked at the tip end of the pusher tube 20. By this, the stent 22 is placed at a desired position.

That is, the stent placement device 11 of the first preferred embodiment of the present invention comprises a holding portion, which is a holding means including the guide tube 15 for holding the stent 22 attached by insertion capable of moving forward/backward in the axial direction, a fixing portion, which is a fixing means including the claw portion 15a and the reduced-diameter portion 15b changing between a locked position and a nonlocked position of the stent 22 when the stent 22 is held by the guide tube, and an operation portion, which is an operating means including a pusher slider 19 having the pusher tube 20 moved/operated to the locked position and the nonlocked position of the stent 22.

In the stent placement device 11 in the first preferred embodiment of the present invention, since the stent 22 is locked and fixed between the claw portion 15a of the guide tube 15 and the tip end of the pusher tube 20, when the stent 22 is inserted at a position deeper than a desired position of the living tissue, advance/retreat control of the stent 22 in the living tissue is made possible.

Also, with the stent placement device 11, when the electrode needle 18 is pulled out at placement of the stent 22 at a desired position, the diameter of the tip end of the guide tube 15 is reduced, and the claw portion 15a is removed from the tip end of the stent 22. Therefore, the user can pull out the guide tube 15, electrode needle 18 while the stent 22 is held by the pusher tube 20 at the placement position, and the user can pull out the pusher tube 20 after placing the stent 22 at the placement position. Moreover, when the user pulls out the stent placement device in the middle of insertion into the treatment instrument insertion channel of the insertion portion of the ultrasonic endoscope device, since the stent 22 is locked by the claw portion 15a of the guide tube 15, the user can pull it out without leaving it in the treatment instrument insertion channel.

Figure 5:
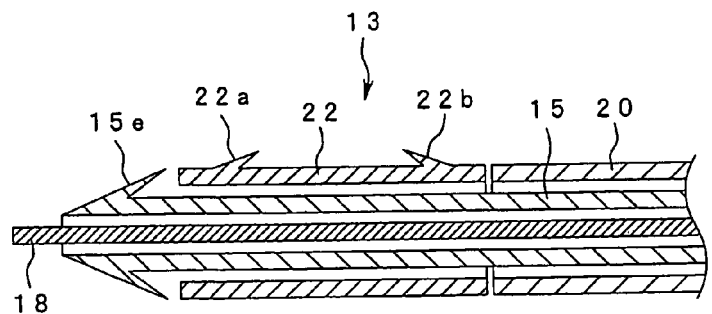
FIG. 5 is a sectional view showing a tip end of an insertion portion of a stent placement device of a second preferred embodiment of the present invention in a state where a stent is attached at the tip end of the guide tube.
Figure 6:
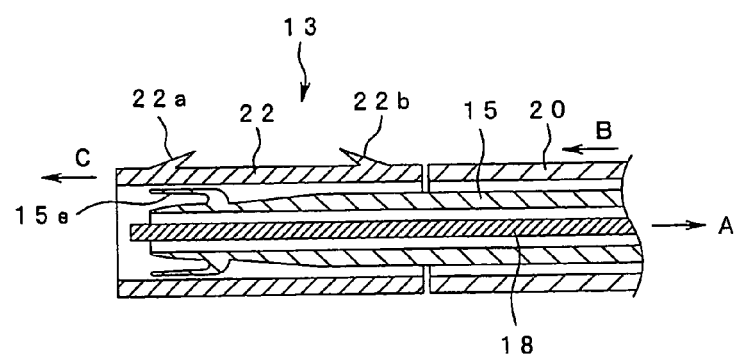
FIG. 6 is a sectional view showing a state where the stent is pushed out of the tip end of the guide tube of the stent placement device in the second preferred embodiment of the present invention.
Figure 7:
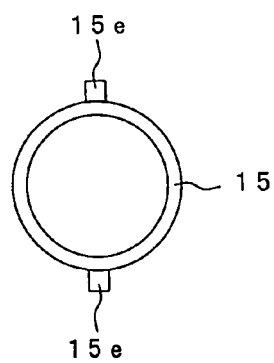
FIG. 7 is a plan view for explaining a shape of the tip end of the guide tube of the stent placement device in the second preferred embodiment of the present invention.
Figure 8:
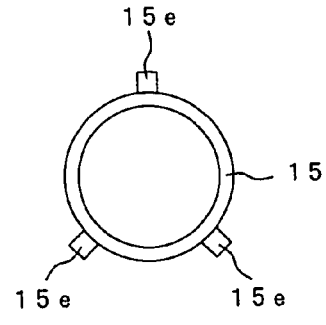
FIG. 8 is a plan view for explaining a shape of the tip end of the guide tube of the stent placement device in the second preferred embodiment of the present invention.

Next, a stent placement device in a second preferred embodiment of the present invention will be described using FIGS. 5 to 7. FIGS. 5 to 8 show the tip end of the insertion portion of the stent placement device of the second preferred embodiment of the present invention, in which FIG. 5 is a sectional view showing a state where the stent is attached to the tip end of the guide tube, FIG. 6 is a sectional view showing a state where the stent is pushed out from the tip end of the guide tube, FIG. 7 is a plan view for explaining a shape of the tip end of the guide tube, and FIG. 8 shows a second variation, which is a plan view for explaining the shape of the tip end of the guide tube. Note that the same portions as the construction in the first preferred embodiment shown in FIGS. 1 to 3 are given the same reference numerals and detailed description will be omitted.

The handle portion 12 of the stent placement device 11 in the second preferred embodiment of the present invention has substantially the same construction as that of the handle portion 12 of the stent placement device 11 in the above-mentioned first preferred embodiment and different only in the construction of the tip end of the guide tube 15 of the insertion portion 13.

The tip end of the guide tube 15 of the stent placement device 11 of this preferred embodiment is provided with, as shown in FIG. 5, the turned-up portion 15e for locking the tip end of the stent 22 attached by insertion on the outer circumference of the tip end of the guide tube 15.

This turned-up portion 15e is formed to be deformed when a force more than prescribed is applied. Moreover, the turned-up portion 15e may be, as shown in FIG. 7, two turned-up portions 15e at opposing positions or may be one or three turned-up portions 15e at an interval of 120 degrees as shown in FIG. 8 when seen from the tip end of the guide tube 15. By providing these plural turned-up portions 15e, a locking force of the stent 22 can be increased. However, when these plural turned-up portions 15e are provided, the user needs a large pulling force to deform the turned-up portions 15e when pulling out.

In the stent placement device 11 with this construction, as shown in FIG. 5, the stent 22 is attached by insertion to the tip end of the guide tube 15 to be locked between the turned-up portion 15e and the tip end of the pusher tube 20. The user inserts the guide tube 15, stent 22, pusher tube 20 into an opening drilled by the electrode needle 18 in the living tissue, as described in the first preferred embodiment.

When adjusting a position of the stent 22 inserted into the living tissue, the user can make adjustment while locking the stent 22 at the turned-up portion 15e of the guide tube 15 and the tip end of the pusher tube 20, and drop of the stent 22 into the living tissue can be prevented.

When the stent 22 is inserted into a position of a target portion, as shown in FIG. 6, the user further pushes out the pusher tube 20 in the arrow B direction in this figure. Then, the turned-up portion 15e of the guide tube 15 is deformed by pushing-out of the pusher tube 20, and the stent 22 is pushed out in the arrow C direction in this figure from the tip end of the guide tube 15 and placed in the living tissue.

Alternatively, other than the above operation, when the user pulls out the guide tube 15 and the electrode needle 18 in the arrow A direction while the position of the pusher tube 20 is fixed, the turned-up portion 15e of the guide tube 15 is deformed by the stent 22, and the guide tube 15 can be pulled out of the stent 22.

That is, the stent placement device 11 of the second preferred embodiment comprises a holding portion, which is a holding means including the guide tube 15 for holding the stent 22 attached by insertion capable of moving forward/backward in the axial direction, a fixing portion, which is a fixing means including the turned-up portion 15e deformed between the locked position and the nonlocked position of the stent 22 when the stent 22 is held by the guide tube 15, and an operation portion, which is an operation means including the pusher tube 20 which can operate the stent 22 to the locked position and the nonlocked position through the stent 22.

With the stent placement device 11 of the second preferred embodiment, as with the above-mentioned first preferred embodiment, advance/retreat adjustment of the stent 22 is made possible in the living tissue. Also, the user can place the stent 22 at a desired position by deformation of the turned-up portion 15e of the guide tube 15 by the pushing-out force applied by the pusher tube 20 to the stent 22.

Also, when pulling out the stent placement device 11 in the middle of insertion into the treatment instrument insertion channel of the insertion portion of the ultrasonic endoscope device, the user can pull it out without leaving it in the treatment instrument insertion channel since the stent 22 is locked by the turned-up portion 15e of the guide tube 15.

Figure 9:
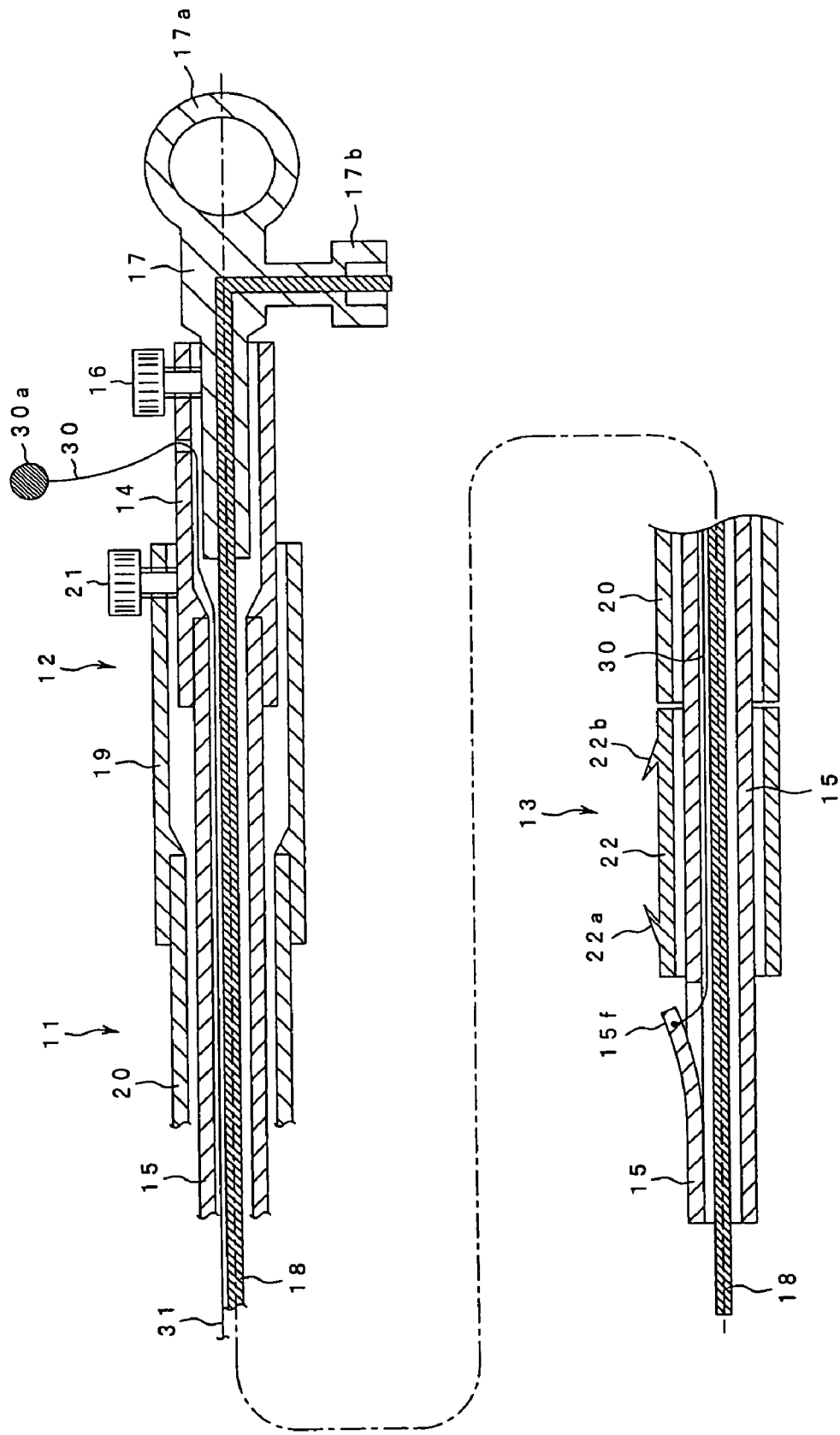
FIG. 9 is a sectional view showing a construction of a stent placement device of a third preferred embodiment of the present invention.
Figure 10:
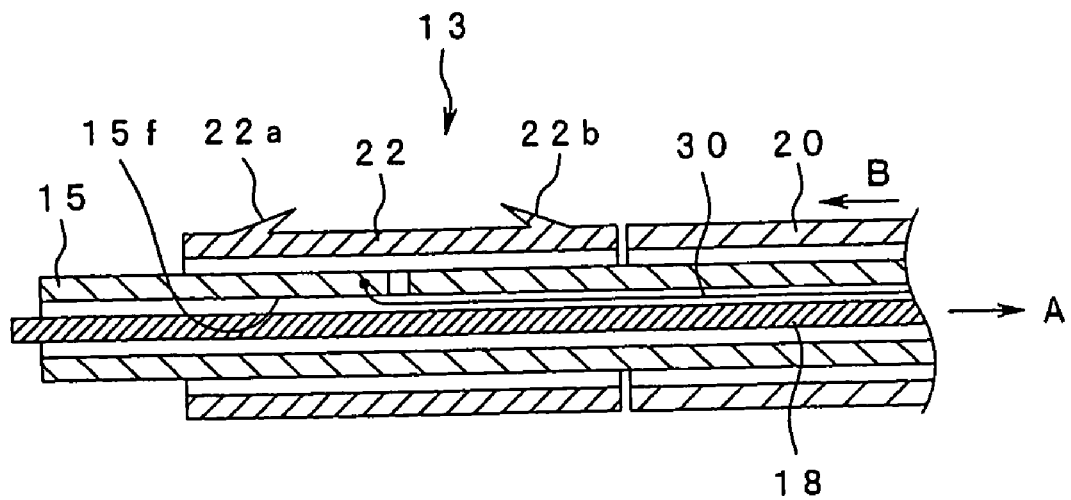
FIG. 10 is a sectional view showing placement operation of a stent by the stent placement device of the third preferred embodiment of the present invention.

Next, a stent placement device of a third preferred embodiment of the present invention will be described using FIGS. 9 and 10. FIGS. 9 and 10 relate to a stent placement device of the third preferred embodiment of the present invention, in which FIG. 9 is a sectional view showing a construction of the stent placement device of the third preferred embodiment, and FIG. 10 is a sectional view showing a placement operation of the stent by the stent placement device of the third preferred embodiment of the present invention. Note that the same portions as the construction in the first preferred embodiment shown in FIGS. 1 to 3 are given the same reference numerals and detailed description will be omitted.

The stent placement device 11 of the third preferred embodiment of the present invention is substantially the same as the stent placement device 11 of the above-mentioned first preferred embodiment and different only in the construction at the tip end of the guide tube 15 of the insertion portion 13.

The tip end of the guide tube 15 of the insertion portion 13 of the stent placement device 11 in this preferred embodiment is, as shown in FIG. 9, provided with a raiser edge unit 15f for locking the tip end of the stent 22 attached by insertion on the outer circumference on the tip end of the guide tube 15.

This raiser edge unit 15f is formed by cutting and raising a side face of the guide tube 15 substantially in a rectangular shape. The raiser edge unit 15f is formed so that it is raised outward of the guide tube 15 all the time.

Moreover, at an upper part of raised portion of the raiser edge unit 15f, a tip end of a pulling thread 30 is attached and fixed. This pulling thread 30 is inserted from the inner circumference of the guide tube 15 to the inner circumference of the handle main body 14 and guided outside of the handle main body 14 through a pulling thread hole provided at the base end side of the handle main body 14.

A pulling knob 30a is provided at the base end of the pulling thread 30 guided out of the handle main body 14. When the pulling thread 30 is pulled through the pulling knob 30a, the raiser edge unit 15f is inclined from the state raised from the side face of the guide tube 15 to a face flush with the side face of the guide tube 15 and accommodated.

That is, the raiser edge unit 15f of the guide tube 15 is, as shown in FIG. 9, raised outward of the guide tube 15 all the time. In this state, the stent 22 attached by insertion on the tip end of the guide tube 15 is locked between the raiser edge unit 15f and the tip end of the pusher tube 20.

In the so-constructed stent placement device 11, as shown in FIG. 9, the stent 22 is attached by insertion at the tip end of the guide tube 15. And while the stent 22 is locked between the raiser edge unit 15f and the tip end of the pusher tube 20, the user inserts the guide tube 15, stent 22 and pusher tube 20 into an opening drilled by the electrode needle 18 in the living tissue.

The user can adjust the position of the stent 22 inserted into the living tissue while the stent 22 is locked by the raiser edge unit 15f of the guide tube 15 and the tip end of the pusher tube 20. Therefore, the stent placement device 11 of this preferred embodiment can prevent drop of the stent 22 into the living tissue.

And when the user inserts the stent 22 to a position of a target portion, as shown in FIG. 10, the user pulls the pulling thread 30 in the arrow A direction. Then, the raiser edge unit 15f is accommodated in the side face of the guide tube 15. Next, the user pushes out the pusher tube 20 in the arrow B direction in this figure from the state where the raiser edge unit 15f is accommodated. Then, the stent 22 is pushed out of the tip end of the guide tube 15 by the pusher tube 20 and placed in the living tissue.

Alternatively, other than the above-mentioned operation, the user can pull the stent 22 out of the guide tube 15 by accommodating the raiser edge unit 15f of the guide tube 15 by the pulling thread 30 and pulling out the guide tube 15 while the position of the pusher tube 20 is fixed.

That is, the stent placement device 11 of this preferred embodiment comprises a holding portion, which is a holding means including the guide tube 15 for holding the stent 22 attached by insertion capable of moving forward/backward in the axial direction, a fixing portion, which is a fixing means including the raiser edge unit 15f moved to be raised and accommodated between the locked position and the nonlocked position of the stent 22 when the stent 22 is held by the guide tube, and an operation portion, which is an operation means including the pusher tube 20 for moving operation of the stent 22 to the locked position and the nonlocked position and the pulling thread 30.

With the stent placement device 11 of the third preferred embodiment of the present invention, as with the above-mentioned first preferred embodiment, advance/retreat adjustment of the stent 22 is made possible in the living tissue. Also, the user can place the stent 22 at a desired position by pushing-out operation by the pusher tube 20 after accommodating the raiser edge unit 15f of the guide tube 15 by the pulling thread 30.

Also, when pulling out the stent placement device 11 in the middle of insertion into the treatment instrument insertion channel of the insertion portion of the ultrasonic endoscope device, the user can pull it out without leaving it in the treatment instrument insertion channel, since the stent 22 is locked by the raiser edge portion 15f of the guide tube 15.

Figure 11:
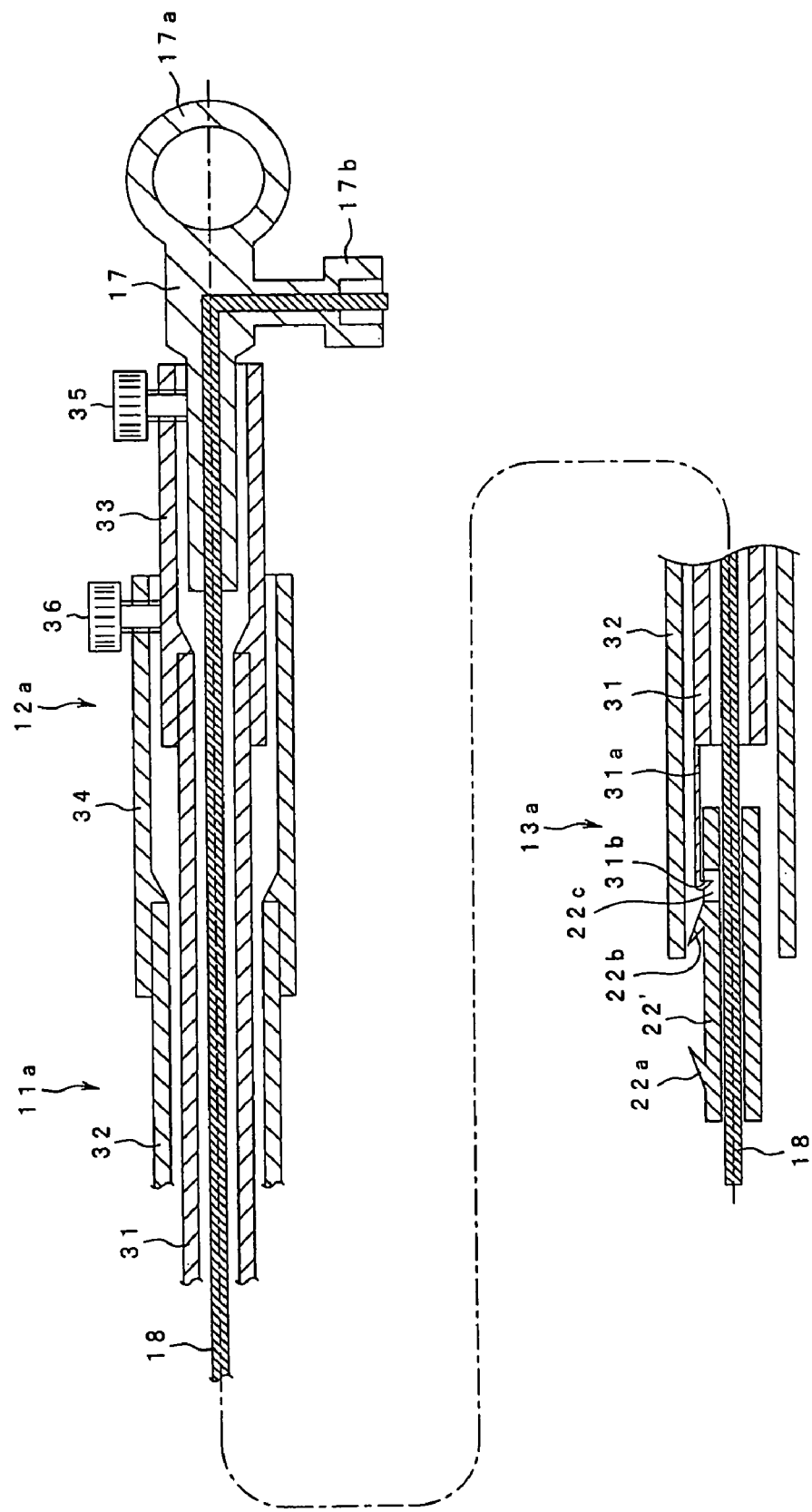
FIG. 11 is a sectional view showing a construction of a stent placement device of a fourth preferred embodiment of the present invention.
Figure 12:
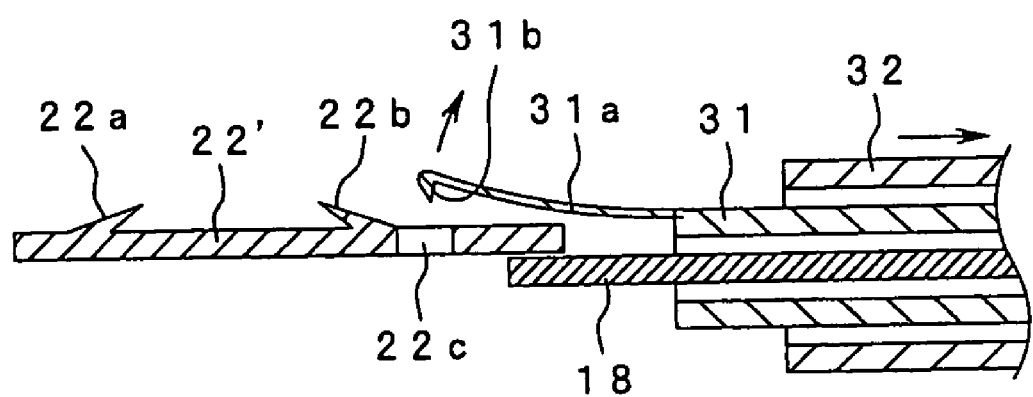
FIG. 12 is a sectional view showing placement operation of a stent by the stent placement device of the fourth preferred embodiment of the present invention.

Next, a stent placement device in a fourth preferred embodiment of the present invention will be described using FIGS. 11 and 12. FIGS. 11 and 12 relates to a stent placement device of the fourth preferred embodiment of the present invention, in which FIG. 11 is a sectional view showing a construction of the stent placement device, and FIG. 12 is a sectional view showing placement operation of the stent. In the following description, the same portions as the construction in the first preferred embodiment shown in FIGS. 1 to 3 are given the same reference numerals and detailed description will be omitted.

A stent placement device 11a of the fourth preferred embodiment of the present invention comprises a handle portion 12a and an insertion portion 13a.

The handle portion 12a comprises a handle main body 33 with a tip end to which a base end of a lock tube 31 is fixed, the electrode slider 17 to which the electrode needle 18 inserted into the lock tube 31 from the rear end of the handle main body 33 is fixed, and a release slider 34 with a tip end to which a base end of a release tube 32 loosely fitted on an outer circumference of the lock tube 31 is fixed and loosely fitted on an outer circumference of the handle main body 33 capable of moving forward/backward.

The handle main body 33 is provided with an electrode lock screw 35 for fixing the electrode slider 17. The release slider 34 is provided with a release lock screw 36 for fixing the release slider 34 to the handle main body 33. The electrode slider 17 is provided with the knob portion 17a and the connector portion 17b.

The insertion portion 13a includes the electrode needle 18 inserted in an inner circumference of the lock tube 31 capable of moving forward/backward with the base end fixed to the handle main body 33, the release tube 32 loosely fitted on the outer circumference of the lock tube 31 capable of moving forward/backward, and a stent 22' attached by insertion on the outer circumference at the tip end of the electrode needle 18 capable of moving forward/backward and located at the tip end of the lock tube 31.

On the lock tube 31, a lock piece 31a in a tongue piece state is formed extending from the tip end of the lock tube 31 in the axial direction. The lock piece 31a is provided with a hook portion 31b at the tip end and is urged outward from outside of the lock tube 31 all the time.

On the other hand, at the rear end side of the stent 22', an opening 22c is provided into which the hook portion 31b of the lock piece 31a of the lock tube is attached by insertion.

In the so-constructed stent placement device 11a, when it is to be inserted into a body cavity, as shown in FIG. 11, after the stent 22' is attached by insertion on the outer circumference at the tip end of the electrode needle 18, the release tube 32 is slid so that the hook portion 31b of the lock piece 31a of the lock tube 31 is attached by insertion in the opening 22c of the stent 22'. That is, the stent 22' is brought into the state held by the hook portion 31b of the lock piece 31a of the lock tube 31 pressed down by the release tube 32.

In this state, the insertion portion 13a is inserted into the body cavity, and the stent 22' and the release tube 32 are inserted into a puncture needle hole generated by the electrode needle 18 in the living tissue. Since the stent 22' is pressed down by the release tube 32, adjustment of placement position to a target portion in the living tissue is made possible.

As the placement operation of the stent 22' after being inserted to the placement position of the target portion in the living tissue, as shown in FIG. 12, the release slider 34 is slid/operated to slide the release tube 32 to the handle portion 12 side in the arrow direction in this figure, and the lock piece 31a is urged outward to the outside of the lock tube 31.

That is, when the release tube 32 pressing down the lock piece 31a of the lock tube 31 is slid, the lock piece 31a is sprung up outward of the lock tube 31, and the hook portion 31b of the lock piece 31a is detached from the opening 22c of the stent 22'. When the user slides the lock tube 31 in this state, the stent 22' is pushed out of the electrode needle 18 at the tip end of the lock tube 31 and can be placed at the position of the target portion.

Also, when the insertion operation into the treatment instrument insertion channel of the insertion portion of the ultrasonic endoscope device is stopped, since the stent 22' is held by the lock piece 31a of the lock tube 31 pressed down by the release tube 32, the stent 22' is not left in the treatment instrument insertion channel.

That is, the stent placement device 11a of the fourth preferred embodiment comprises a holding portion, which is a holding means including the lock tube 31 for holding the stent 22' attached by insertion capable of moving forward/backward in the axial direction, a fixing portion, which is a fixing means including the lock piece 31a deformed between the locked position and the nonlocked position of the stent 22' and the release tube 32 when the stent 22' is held by the lock tube 31, and an operation portion, which is an operation means including the lock tube 31 and the release tube 32 operating the stent 22' between the locked position and the nonlocked position.

With the stent placement device 11a of the fourth preferred embodiment of the present invention, advance/retreat adjustment of the stent 22' in the living tissue is made possible as with the above-mentioned first preferred embodiment. Also, when the user places the stent 22' at a desired position, by releasing lock between the lock piece 31a of the lock tube 31 and the stent 22' using the release tube 32, pushing-out placement by the lock tube 31 can be performed. Also, when pulling out the stent placement device 11a in the middle of insertion to the treatment instrument insertion channel of the insertion portion of the ultrasonic endoscope device, the user can pull out the stent 22' without leaving it in the treatment instrument insertion channel since the stent 22' is locked by the lock piece 31a of the lock tube 31.

Figure 13:
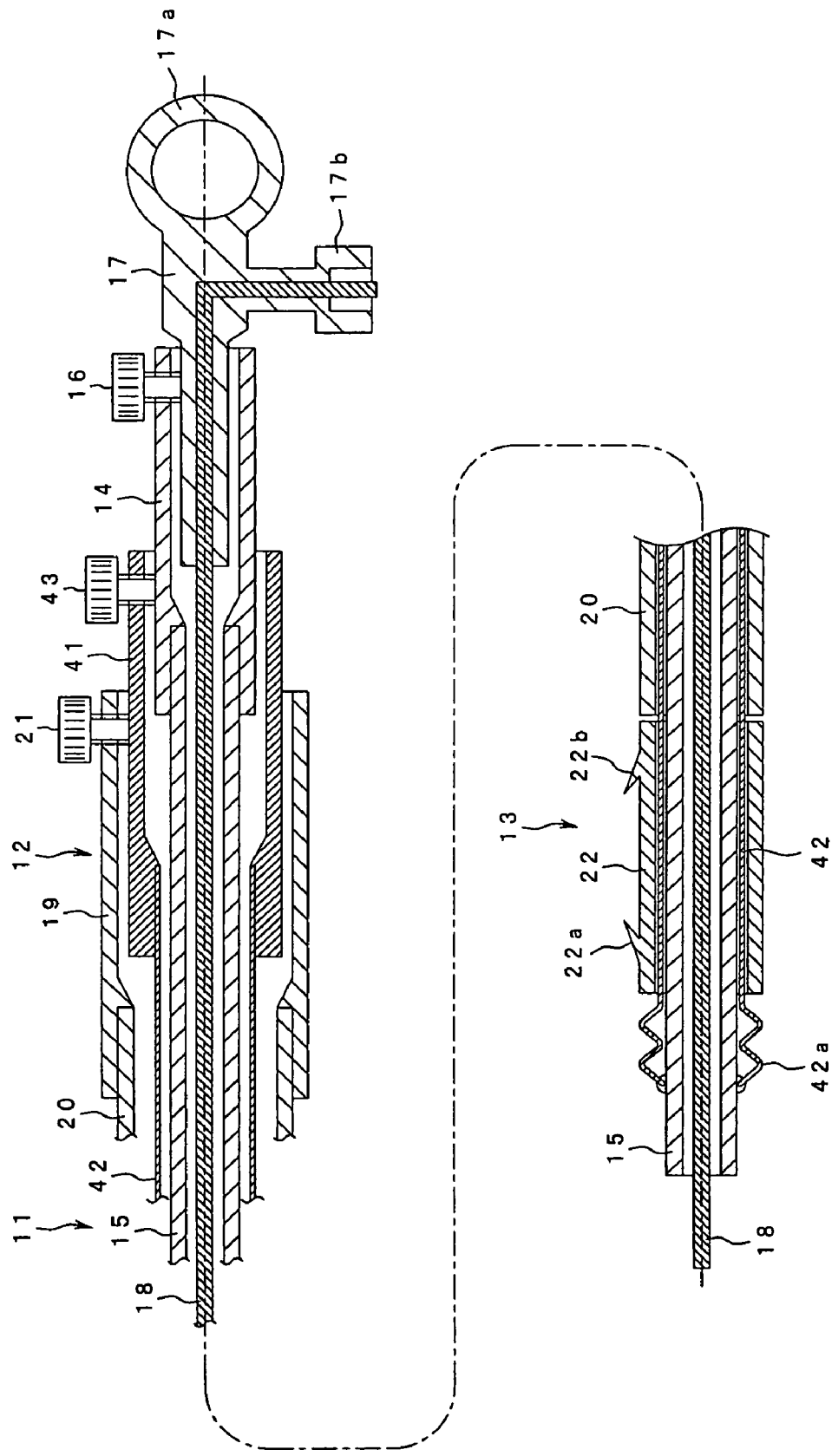
FIG. 13 is a sectional view showing a construction of a stent placement device of a fifth preferred embodiment of the present invention.
Figure 14:
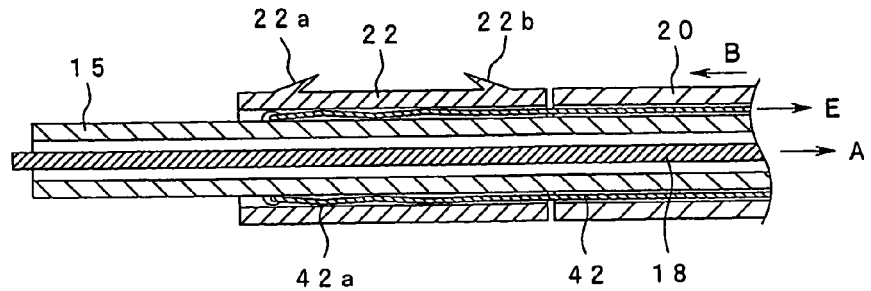
FIG. 14 a sectional view showing a placement operation of a stent by the stent placement device of the fifth preferred embodiment of the present invention.

Next, a stent placement device of a fifth preferred embodiment of the present invention will be described using FIGS. 13 and 14. FIGS. 13 and 14 relates to a stent placement device of the fifth preferred embodiment of the present invention, in which FIG. 13 is a sectional view showing a construction of the stent placement device and FIG. 14 is a sectional view showing a placement operation of the stent by the stent placement device. In the following description, the same portions as the construction in the first preferred embodiment shown in FIGS. 1 to 3 are given the same reference numerals and detailed description will be omitted.

In the stent placement device 11 of the fifth preferred embodiment of the present invention, a difference from the above-mentioned stent placement device 11 of the first preferred embodiment is that a bellows slider 41 is provided capable of moving forward/backward between the handle main body 14 of the handle portion 12 and the pusher slider 19, and a bellows tube 42 is provided capable of moving forward/backward between the guide tube 15 of the insertion portion 13 and the pusher tube 20.

At a tip end of the bellows slider 41, a base end of the bellows tube 42 is fixed. Also, at a rear end of the bellows slider 41, a bellows lock screw 43 is provided. The bellows tube 42 is provided with a bellows portion 42a at its tip end. A tip end of the bellows tube 42 is fixed to an outer circumference at the tip end of the guide tube 15. That is, when the bellows slider 41 is slid with respect to the handle main body 14, the bellows tube 42 is slid and the bellows portion 42a is expanded/contracted.

On the outer circumference of the bellows tube 42, the stent 22 is attached by insertion. The stent 22 is attached by insertion so that it is locked between the bellows portion 42a in the contracted state and the tip end of the pusher tube 20. That is, when the bellows portion 42a is brought into a contracted state, an outer diameter of the bellows portion 42a is increased, and the stent 22 is locked between the bellows portion 42a and the tip end of the pusher tube 20, while when the bellows portion 42a is brought into an expanded state, the outer diameter of the bellows portion 42a is decreased, and the stent 22 is made capable of sliding movement outside the bellows portion 42a.

In the so-constructed stent placement device 11, as shown in FIG. 13, the stent 22 is attached by insertion on the bellows tube 42 on the tip end of the guide tube 15, and the bellows portion 42a is brought into the contracted state. In the state where the stent 22 is locked by the tip end of the pusher tube 20, the user inserts the stent 22 into an opening drilled by the electrode needle 18 in the living tissue together with the guide tube 15, bellows tube 42 and the pusher tube 20.

With the stent placement device 11 of this preferred embodiment, when adjusting the position of the stent 22 inserted into the living tissue, since the adjustment can be carried out in the state where the stent 22 is locked by the bellows portion 42a and the tip end of the pusher tube 20, drop of the stent 22 into the living tissue can be prevented.

When the user inserts the stent 22 into a position of the target portion and, as shown in FIG. 14, pulls the bellows tube 42 in a direction of an arrow E, the bellows portion 42a is brought into the expanded state. When the user pushes out the pusher tube 20 in the arrow B direction in this figure from the state where the bellows portion 42a is expanded, the stent 22 is pushed out by the pusher tube 20 from the tip end of the guide tube 15 via the bellows portion 42a and placed in the living tissue.

Alternatively, other than the above operation, when the user pulls out the guide tube 15 and the bellows tube 42 in the state where the bellows portion 42a is expanded with the pusher tube 20 fixed in place, the stent 22 can be pulled out of the bellows tube 42 and the guide tube 15.

That is, the stent placement device 11 of this preferred embodiment comprises a holding portion, which is a holding means including the bellows tube 42 for holding the stent 22 attached by insertion capable of moving forward/backward in the axial direction, a fixing portion, which is a fixing means including the bellows portion 42a deformed between the locked position and the nonlocked position of the stent 22 when the stent 22 is held by the bellows tube 42, and an operation portion, which is an operation means including the pusher tube 20 for moving operation of the stent 22 to the locked position and the nonlocked position.

With the stent placement device 11 of the fifth preferred embodiment of the present invention, as in the above-mentioned first preferred embodiment, adjustment of advance/retreat of the stent 22 is made possible in the living tissue. Also, when placing the stent 22 at a desired position, the user can push out and place the stent 22 by advance/retreat operation of the bellows tube 42 and the pusher tube 20. Also, when pulling out the stent placement device 11 in the middle of insertion into the treatment instrument insertion channel of the insertion portion of the ultrasonic endoscope device, the user can also pull out the stent 22 without leaving it in the treatment instrument insertion channel since the stent 22 is locked by the bellows portion 42a of the bellows tube 42.

Figure 15:
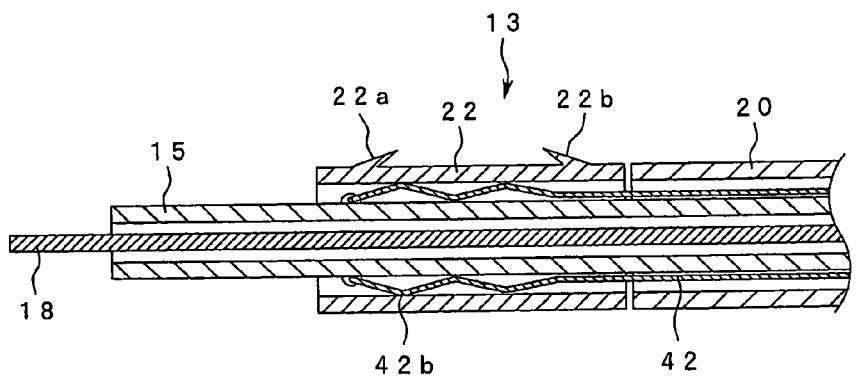
FIG. 15 is a sectional view showing a construction at the tip end of an insertion portion of a stent placement device of a sixth preferred embodiment of the present invention in a state where the stent is locked at the tip end of the insertion portion.
Figure 16:
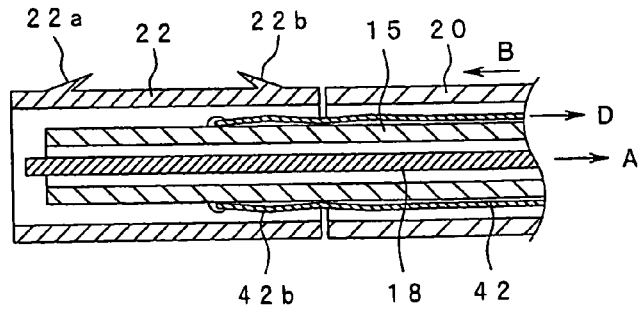
FIG. 16 is a sectional view showing a state where the stent is placed from the tip end of the insertion portion of the stent placement device of the sixth preferred embodiment of the present invention.

Next, a stent placement device of a sixth preferred embodiment of the present invention will be described using FIGS. 15 and 16. FIGS. 15 and 16 relate to the stent placement device of the sixth preferred embodiment of the present invention, both of them being sectional views showing construction at the tip end of an insertion portion of the stent placement device of this preferred embodiment, in which FIG. 15 shows a state where the stent is locked at the tip end of the insertion portion, while FIG. 16 shows a state where the placement operation is carried out for the stent to be placed from the tip end of the insertion portion. In the following description, the same portions as the construction in the fifth preferred embodiment shown in FIGS. 13 and 14 are given the same reference numerals and detailed description will be omitted.

The stent placement device 11 of the sixth preferred embodiment of the present invention is substantially the same as the stent placement device 11 of the above-mentioned fifth preferred embodiment. A difference is that with regard to the bellows tube 42 provided between the guide tube 15 of the insertion portion 13 and the pusher tube 20, the bellows portion 42b is located on the inner circumference of the stent 22 attached by insertion at the tip end of the guide tube 15.

That is, the bellows portion 42b of the bellows tube 42 is arranged so that the bellows portion 42b is contracted within the inner circumference of the stent 22 attached by insertion. When the bellows portion 42b is contracted, an outer diameter of the bellows portion 42b is increased, the bellows portion 42b is strongly pressed on the inner circumference of the stent 22, and the stent 22 is brought into the lock state where the stent 22 can not slide.

Moreover, when the bellows portion 42b is expanded, the outer diameter of the bellows portion 42b is decreased, a pressure of the bellows portion 42b on the inner circumference of the stent 22 is lowered, and the stent 22 is brought into the unlock state where the stent 22 can slide from the bellows portion 42b and the guide tube 15.

In the so-constructed stent placement device 11, as shown in FIG. 15, the stent 22 is attached by insertion to the bellows tube 42 at the tip end of the guide tube 15. The user locks the stent 22 in the state where the bellows portion 42b is contracted and inserts the stent 22 together with the guide tube 15, the pusher tube 20 into an opening drilled by the electrode needle 18 in the living tissue.

With the stent placement device 11 of this preferred embodiment, since the position of the stent 22 inserted into the living tissue can be controlled with the stent 22 locked by the bellows portion 42b, drop of the stent 22 into the living tissue can be prevented.

When the stent 22 is inserted to a position of a target portion, the user pulls the bellows tube 42 in the arrow D direction to expand the bellows portion 42b as shown in FIG. 16. When the pusher tube 20 is pushed out in the arrow B direction in this figure from the state where the bellows portion 42b is expanded, the stent 22 is pushed out of the tip end of the guide tube 15 via the bellows portion 42b by the pusher tube 20 and placed in the living tissue.

Or, when the guide tube 15 and the bellows tube 42 with the expanded bellows portion 42b are pulled out with the pusher tube 20 fixed in place, the stent 22 is pulled out of the guide tube 15.

That is, the stent placement device 11 of the sixth preferred embodiment comprises a holding portion, which is a holding means including the bellows tube 42 for holding the stent 22 attached by insertion capable of moving forward/backward in the axial direction, a fixing portion, which is a fixing means including the bellows portion 42b deformed between the locked position and the nonlocked position of the stent 22 when the stent 22 is held by the bellows tube 42, and an operation portion, which is an operation means including the pusher tube 20 for operation of the stent to the locked position and the nonlocked position.

With the stent placement device 11 of the sixth preferred embodiment of the present invention, as in the above-mentioned first preferred embodiment, adjustment of advance/retreat of the stent 22 is made possible in the living tissue. Also, when placing the stent 22 at a desired position, the user can push out and place the stent 22 by advance/retreat operation of the bellows tube 42 and the pusher tube 20.

Also, when pulling out the stent placement device 11 in the middle of insertion into the treatment instrument insertion channel of the insertion portion of the ultrasonic endoscope device, since the stent 22 is locked by the bellows portion 42b of the bellows tube 42, the user can pull out the stent 22 without leaving it in the treatment instrument insertion channel.

In each of the above-mentioned preferred embodiments of the present invention, description was made using the example in which the electrode needle 18 is provided with an electrode at its tip end for generating by radiofrequency power an opening to which the stent 22 is inserted in a living tissue. In place of this electrode needle 18, a needle pipe with a tip end formed sharp may be used.

Figure 17:
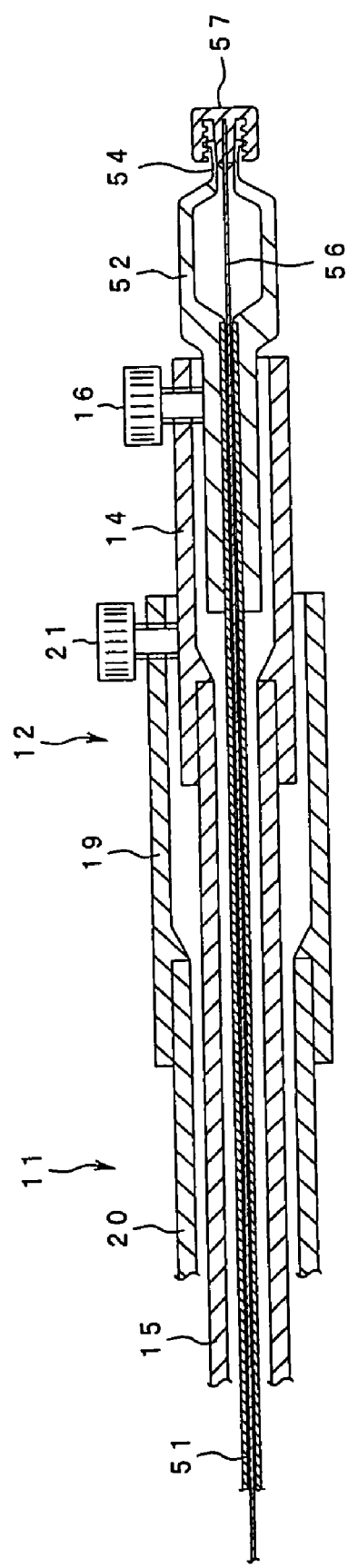
FIG. 17 is a sectional view showing a handle portion of the stent placement device, which is an application example of the preferred embodiment of the present invention.

Construction of the handle portion 12 of the stent placement device 11 using this needle pipe will be described using FIG. 17. FIG. 17 is a sectional view showing the handle portion of the stent placement device, which is an application example of the preferred embodiment of the present invention. In the following description, the same portions as the construction in the first preferred embodiment shown in FIG. 1 are given the same reference numerals and detailed description will be omitted.

A needle pipe slider 52 to which a base end of a needle pipe 15 is fixed is provided on the inner circumference of the handle main body 14. A tip end of the needle pipe 15 is inserted into the inner circumference of the guide tube 15 and moved forward/backward from the tip end of the guide tube 15. A base 54 is provided at a rear end of the needle pipe slider 52. A stylette 56 is inserted through the base 54 through a hollow portion of the needle pipe 51 and moved forward/backward from the tip end of the needle pipe 51.

A stylette knob 57 to be gripped at advance/retreat operation of the stylette 56 and fixed to the base 54 of the needle pipe slider 52 is provided at a base end of the stylette 56. An advance/retreat position of the needle pipe slider 52 is fixed by the electrode lock screw 16 provided at the handle main body 14.

By replacing the electrode needle 18 by an opening including this needle pipe 51 and the stylette 56, the stent placement device 11 described in the above-mentioned first to sixth preferred embodiments can be generated, which enables similar operation and gives the same advantage.

The stent placement device 11 in each of the above-mentioned preferred embodiments has such advantages that the stent 22 can be inserted into an opening generated by an opening tool in the living tissue for advance/retreat operation, the stent 22 can be placed exactly at a position of a target portion, and the stent placement device 11 can be operated forward/backward without leaving the stent 22 in the treatment instrument insertion channel irrespective of the shape of the insertion portion of the ultrasonic endoscope device, which improves operability of the stent placement.

By this, according to the stent placement device 11 in each of the above-mentioned preferred embodiments, advance/retreat operation for adjusting a placement position of the stent 22 in the living tissue and advance/retreat operation of the ultrasonic endoscope device in the treatment instrument insertion channel are made possible.

The above described invention is not limited to each of the preferred embodiments but various variations can be made in practice in a range not deviating from the gist of the invention. Moreover, each preferred embodiment includes an invention in various stages, and various inventions can be extracted by appropriately combining disclosed plural components.

For example, even if several components are deleted from all the components shown in each preferred embodiment, the problem described in the problem to be solved by the invention can be solved, and when the effect described in the advantages of the invention is obtained, the construction with the component deleted can be extracted as an invention.

What is claimed is:

1. A stent placement device comprising:
   a stent to be placed in an opening formed in a body cavity;
   a holding portion configured to hold the stent;
   a needle configured to be inserted into the body cavity and inserted and located through the holding portion so as to be movable forward/backward in the axial direction of the holding portion in order to form an opening in the body cavity;
   a tube body adapted to loosely fit on an outer circumference of the holding portion; and
   a lock portion which is provided to the holding portion, is elastically deformable into a state insertable into the stent, locks the stent by deformation with a diameter of the lock portion expanded at a tip end of the tube body and elastically deforms from a state of locking the stent to a state of not locking the stent, wherein
   the tube body, the holding portion or the needle is relatively moved to elastically deform the lock portion from a locked position to a nonlocked position of the stent, to cause the stent to be detached and placed in the body cavity.

2. The stent placement device according to claim 1, wherein the lock portion locks a tip end portion of the stent held by the holding portion and holds the stent between the lock portion and the tube body.

3. The stent placement device according to claim 2, wherein the lock portion is a claw portion provided at a tip end in the axial direction of the holding portion, the holding portion includes at a tip end thereof a plurality of slits formed backward to a predetermined position along the axial direction, the claw portion is pushed up by the needle inserted and located up to the tip end of the holding portion to deform to have an increased diameter and contact the tip end of the stent, thus brought into a locked state holding the stent between the claw portion and the tube body, and the claw portion is deformed in an inner diameter direction of the stent to have a reduced diameter by operating the needle to move backward the holding portion, to bring the stent into a nonloeked state.

4. A stent placement device comprising:

a holding portion for holding a stent to be placed in an opening formed in a body cavity such that the stent is movable forward/backward in the axial direction;

a fixing portion which is provided at a tip end of the holding portion and is changeable between a position at which the stent is locked and a position at which the stent is not locked when the stent is held by the holding portion; and an operation portion for operating change of the fixing portion between the locked position and the nonlocked position of the stent, wherein the fixing portion includes a lock portion for locking a tip end portion of the stent held by the holding portion in the axial direction, and the lock portion of the fixing portion includes a claw portion provided at the tip end of the holding portion in the axial direction and a reduced-diameter tip end portion whose diameter at the tip end having the claw portion can be reduced with respect to the central axis.

5. A stent placement device comprising:

an opening tool to be inserted into a body cavity for forming an opening in an organ in the body cavity;

a stent to be attached and placed in the opening formed by the opening tool;

a holding portion into which the opening tool is inserted so as to be within the inner circumference and which holds the stent movably forward/backward in the axial direction on an outer circumference of the holding portion;

a fixing portion which is provided at a tip end of the holding portion and is changeable between a position at which the stent is locked and a position at which the stent is not locked when the stent is held by the holding portion; and an operation portion for operating the change of the fixing portion between the locked position and the nonlocked position of the stent, wherein the fixing portion includes a lock portion for locking a tip end portion of the stent held by the holding portion in the axial direction, and the lock portion of the fixing portion includes a claw portion provided at a tip end of the holding portion in the axial direction and a reduced-diameter tip end portion whose outer diameter at the tip end having the claw portion can be reduced with respect to the central axis in the axial direction.

\* \* \* \* \*